United States Patent [19]

Abushanab et al.

[11] Patent Number: 5,703,084
[45] Date of Patent: Dec. 30, 1997

[54] ADENOSINE DEAMINASE INHIBITORS

[75] Inventors: Elie Abushanab, Peacedale, R.I.; Palle V. P. Pragnacharyulu, Bridgton, Mo.

[73] Assignee: The Board of Governors for Higher Education, State of Rhode Island and Providence Plantations, Providence, R.I.

[21] Appl. No.: 680,413

[22] Filed: Jul. 15, 1996

[51] Int. Cl.$^6$ ............................ A61K 31/52; C07D 473/18
[52] U.S. Cl. ................................... 514/261; 541/277
[58] Field of Search ........................... 544/277; 514/261

[56] References Cited

U.S. PATENT DOCUMENTS 5,491,146  2/1996  Abushanab ........................... 514/261

*Primary Examiner*—C. Warren Ivy
*Assistant Examiner*—Evelyn Huang
*Attorney, Agent, or Firm*—Samuels, Gauthier, Stevens & Reppert

[57] ABSTRACT

This invention disclosed (2S,3R)-3(6-aminopurin-9-yl) aralkan-2-ols, a novel class of adenine derivatives (also called 9-aralkyladenines, ARADS), which have been shown to inhibit the enzyme adenosine deaminase at therapeutically useful levels. The relevant inhibitory constant ($K_i$) values are in the range of $10^{-7}$-$10^{-10}$M. These compounds with potencies in this range can reversibly inhibit ADA in an effective manner, without permanently deactivating the enzyme. ADA inhibitors that have similar biological profiles have been shown to be of therapeutic value when used to protect heart muscle against ischemic damage.

12 Claims, 1 Drawing Sheet

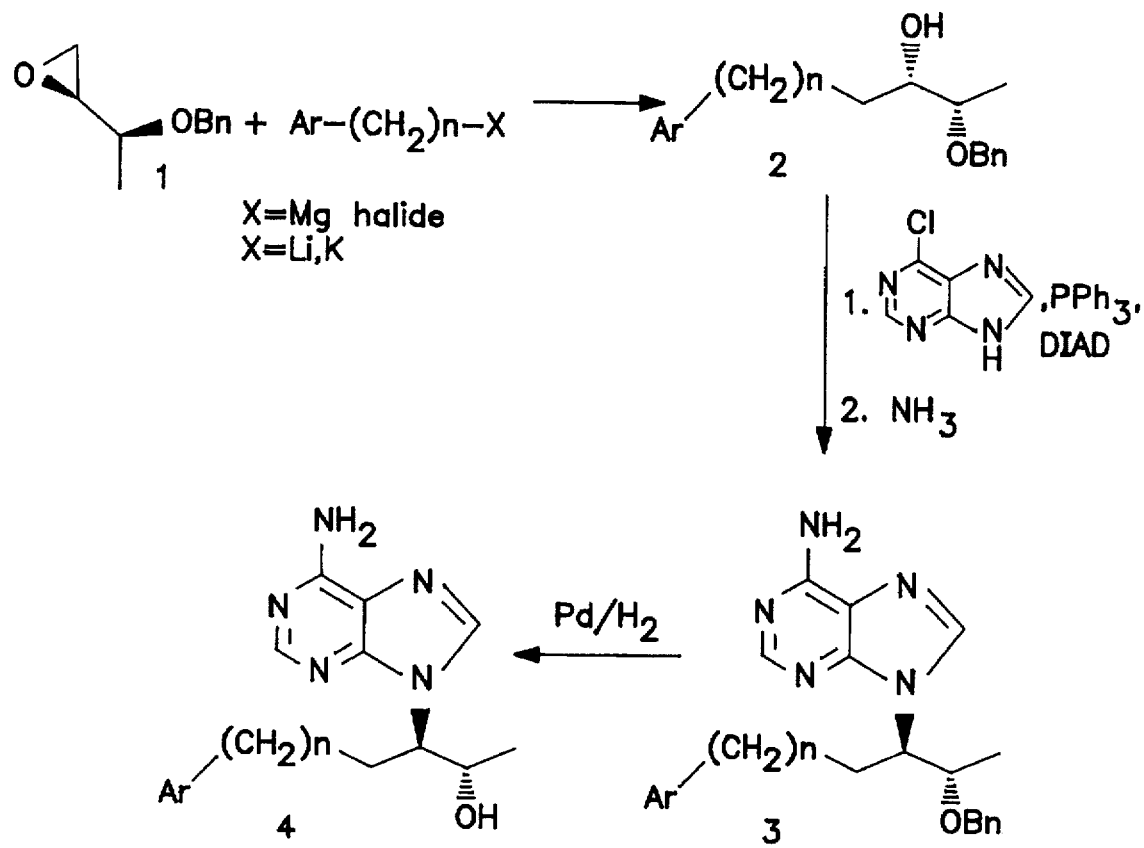

5,703,084

1
ADENOSINE DEAMINASE INHIBITORS
BACKGROUND OF THE INVENTION

This invention is in the field of chemistry and pharmacology and relates to drugs that can inhibit adenosine deaminase. Such drugs can be used to reduce the metabolic degradation of cancer and viral chemotherapeutic agents.

The enzyme adenosine deaminase (ADA, also known as adenosine aminohydrolase) is designated as E.C.3.5.4.4. in the international classification system. It is a catabolic enzyme which converts adenosine and 2'-deoxyadenosine to the corresponding inosine and 2'-deoxyinosine by replacing the amino group at the sixth position in adenine with a hydroxyl group.

ADA can also degrade a number of other nucleosides that are used in cancer and/or viral chemotherapy. Therefore, ADA inhibitors can be used as adjuncts (i.e., as secondary agents to increase the effectiveness of a primary drug) to prolong the metabolic half-lives of drugs in cancer and viral chemotherapy. ADA inhibitors can also be used to artificially create ADA deficiencies which are of interest to research as biochemical tools.

There are a number of known ADA inhibitors both of natural and synthetic origin. Deoxycoformycin (dCF, Pentostatin) is the most potent naturally occurring inhibitor. It is a 2'-deoxynucleoside with a $K_i$ value of $2.5 \times 10^{-12}$ M. This potent activity is described as tight-binding because regeneration of the enzyme is extremely slow and the inhibition is sometimes described as irreversible. Pentostatin is in clinical use for the treatment of hairy cell leukemia.

There are also a number of synthetic ADA inhibitors. Among the most important is erythrohydroxynonyl adenine (EHNA) which was discovered by Schaeffer, H. J. and Schwender, C. F., Enzyme Inhibitors XXVI:Bridging Hydrophobic and Hydrophilic Regions on Adenosine Deaminise with Some 9-(2-Hydroxy-3-alkyl)adenines, J. Med. Chem., 17:68, 1974. A difference between EHNA and dCF is the potency of inhibition of the enzyme. EHNA has a Ki value of $10^{-9}$ M which makes it one thousand times less active than dCF. Another major difference between the two drugs is their duration of inhibition of ADA. Unlike dCF, inhibition with EHNA is reversible with a half life of half an hour. This difference is based on the fact that EHNA is apparently metabolized by liver enzymes to oxidized (hydroxylated) metabolites which are excreted in the urine, McConnell, W. R.; el Dareer, S. M.; Hill, D. L., Metabolism and Disposition of erythro-9-(2-Hydroxy-3-nonyl)[$^{14}$C] adenine in the Rhesus Monkey, Drug Metab. Disp., 1980, 8, 5–7; and Lambe, C. U.; Nelson, D. J., Pharmacokinetics on Inhibition of Adenosine Deaminase by erythro-9-(2-Hydroxy-3-nonyl)adenine in CBA Mice, Biochem. Pharmacol., 1983, 31, 5356–539.

Because dCF is a very toxic drug, recent attention has been focused on EHNA since therapy with EHNA is expected to produce the pharmacological effects with reduced toxicity.

The renewed interest in EHNA has stimulated studies to understand the relationship between its structure and activity. This has led to the synthesis of a large number of analogs modified both at the heterocycle (adenine) as well as the aliphatic chain attached to it. Ring modified analogs have shown the need for N-1 but not N-3 in the six-membered ring. On the other hand studies of the alkyl chain which has two chiral carbons at C-2 and C-3 have demonstrated the importance of chirality to biological activity.

The original work by Schaeffer et al. produced a racemic mixture of EHNA and most of the early work was done on this optically inactive material. However, two laboratories have later shown that most of the activity resides in the (+)-2,S,3R erythro isomer. Baker, D. C.; Hawkins, L. D., Synthesis of Inhibitors of Adenosine Deaminase. A Total Synthesis of (+)-erythro-3-(Adenyl-9-yl)-2-nonanol and its Isomers from Chrial Precursors, J. Org. Chem., 1982, 47, 2179–2184; and Bastian, G.; Bessodes, M.; Panzica, R. P.; Abushanab, E.; Chen, S. F.; Stoeckler, J. D.; Parks, Jr., R. E., Adenosine Deaminase Inhibitors. Conversion of a Single Chrial Synthon into erythro-and threo-9-(2-Hydroxy-3-nonyl)adenines, J. Med Chem., 1981, 24, 1383–1385. These findings have spurred the synthesis of EHNA analogs that maintained the same chirality at these two centers, Harriman, G.; Poirot, A.; Abushanab, E.; Midgett, R. M.; Stoeckler, J. Adenosine Deaminase Inhibitors. Synthesis and Biological Evaluation of C1' and Nor-C1' Derivatives of (+)-erythro-9-(2(S)-Hydroxy-3(R)-nonyl)adenine. J. Med. Chem., 1992, 35, 4180.

Most recently, hydroxylated derivatives of (+)-EHNA at positions 8- and 9- in the alkyl chain have been shown to have, in addition to ADA inhibitory activity, Varghese, C.; Sarma, M. S. P.; Palle, V. P.; Abushanab, E.; Li, S. Y.; Stoeckler, J., Adenosine Deaminase Inhibitors. Synthesis and Biological Evaluation of Putative Metabolites of (+)-erythro-9-(2S-Hydroxy-3R-nonyl) adenine, J. Med. Chem., 1994, 37, 3844, a protective effect on the heart muscle against ischemic damage (Abushanab, U.S. Pat. No. 5,491, 146 which patent is hereby incorporated by reference in its entirety into this disclosure). This protective effect has been previously reported for dCF in a cardiovascular and a neuroprotection model.

SUMMARY OF THE INVENTION

The present invention embodies a novel and hitherto unknown class of aralkyl adenines (ARADS) which inhibit ADA reversibly. Some of these derivatives demonstrate, for the first time, greater ADA inhibitory activity than any previously reported synthetic inhibitors. One beneficial use of the ARADS is to slow down the degradation of certain types of useful therapeutic drugs by ADA.

The ARAD analogs described herein can be administered as adjuncts to prolong the half-lives and increase the effectiveness of chemotherapeutic drugs (usually used as anti-cancer or anti-viral agents) that are degraded by ADA. As will be recognized by those skilled in the art, the desired range of Ki values is relatively broad, since candidate compounds can be administered to a patient at any desired level by various routes.

These analogs have an additional therapeutic value when used to protect heart muscle against ischemic damage. Further, it is believed these analogs have utility in the preservation of organs used for transplants.

Included within the family of ARADS useful for the purposes described herein are any isomers (including "threo" isomers), analogs, or salts of the compounds described herein, provided that such isomers, analogs, and salts are functionally effective as ADA inhibitors, and are pharmacologically acceptable. The term "pharmacologically acceptable" embraces those characteristics which make a drug suitable and practical for administration to humans; such compounds must be sufficiently chemically stable to have an adequate shelf life under reasonable storage conditions and they must be physiologically acceptable when introduced into the body by a suitable route of administration. Acceptable salts can include alkali metal salts as well as addition salts of free acids or free bases. Examples of acids which are widely used to form pharmacologically acceptable acid-addition salts include inorganic acids such as hydrochloric acid, sulfuric acid and phosphoric acid, and organic acids such as maleic acid, succinic acid and citric acid. Alkali metal salts or alkaline earth metal salts could include, for example, sodium, potassium, calcium or magnesium salts. All of these salts may be prepared by conventional means. The nature of the salt is not critical, provided that it is non-toxic and does not substantially interfere with the desired activity.

The term "analog" is used herein in the conventional pharmaceutical sense. In chemical terminology, an analog refers to a molecule that structurally resembles a referent molecule but which has been modified in a targeted and controlled manner to replace a certain substituent of the referent molecule with an alternate substituent other than hydrogen. Such analogs are covered by the claims herein only if they satisfy the efficacy requirements disclosed herein, in a manner which does not destroy the desired function of ADA inhibition by the compound at a Ki value in the range of about $10^{-7}$ to about $10^{-10}$.

Administration of the compounds of this invention to humans or animals can be any technique capable of introducing the compounds into the bloodstream, including oral administration or via intravenous or intramuscular injections. The active compound is usually administered in a pharmaceutical formulation such as in a liquid carrier for injection, or in capsule, table, or liquid form for oral ingestion. Such formulations may comprise a mixture of one or more active compounds mixed with one or more pharmaceutically acceptable carriers or diluents. If desired, other therapeutic agents (such as anti-cancer or anti-viral nucleoside analogs) may also be present in an injectable formulation or an ingestible capsule, table, or liquid.

The invention also embodies syntheses that can be used to prepare these compounds and their analogs containing adenine modified and aryl substituted (2S,3R)-3-(6-aminopurin-9-yl) alkan-2-ol.

The invention comprises various erythro-(2S,3R)-3-(6-aminopurin-9-yl) aralkan-2-ols (ARADS) which can also be called 9-aralkyladenines. The invention teaches synthetic reagents and general methods that can be used to create these and other ARADS which contain aromatic substituents including alkyl, halide, hydroxy, acid, ester, ether, amine, azide or other moieties at the alkyl as well as the aryl portion of the chain. Analogs can also be modified in the adenine structure if desired.

The ARADS described herein have been shown to inhibit adenosine deaminase (ADA) at therapeutically useful levels. The relevant Ki values are in the range of $10^{-8}$ to $10^{-9}$M which is within a desired range of $10^{-7}$ to $10^{-10}$M. ARADS that have potencies within this range can effectively inhibit ADA activity on a reversible basis without permanently poisoning (irreversibly binding to) the enzyme.

BRIEF DESCRIPTION OF THE DRAWINGS

The FIGURE is a general synthesis scheme for ARADS.

DESCRIPTION OF THE PREFERRED EMBODIMENT(S)

This invention discloses a new series of (2S,3R)-3-(6-aminopurin-9-yl) arylalkan-2-ols (also, called 9-aralkyladenines, ARADS), where the alkyl group is composed of 4-8 carbon atoms having a hydroxy group at carbon #2 with (S) chirality and an adenine ring attached through the nitrogen at position #9 to carbon #3 with (R) chirality. The terminal carbon of this alkyl chain is attached to an aromatic ring (phenyl, napththyl, thienyl, furanyl, etc.) which ring can be substituted with alkyl, halide, hydroxy, carboxylic acid, ester, ether, azide, amine, etcetera moieties to make useful analogs.

This invention also discloses methods for synthesizing these compounds (ARADS). The method broadly comprises the following steps as shown in the FIGURE:

a. Reacting an epoxide reagent having the desired chiral orientation with an aryl or aralkyl moiety in the form of a Grignard reagent or an alkali metal salt to form an aralkyl chain which has a hydroxyl group at carbon #3.

b. Reacting the hydroxy group at carbon atom #3 with 6-chloropurine under Mitsunobu conditions consisting of triphenylphosphine, diethyl- or diisopropyl azodicarboxylate, in a suitable solvent such as benzene, toluene, THF to form a new compound comprised of a 6-chloropurine ring attached through its nitrogen at #9 to the aralkyl chain at position 3. Alternately this compound can be obtained by constructing the purine ring in a stepwise fashion. This comprises connecting the alcohol to a sulfonate ether and reacting this ester with sodium azide to form an arylalkyl chain substituted at position three with an azido group.

c. Reduction of this azido group by established methodology gives the corresponding amino compound.

When these basic steps have been completed, any additional processing is carried out which is necessary to complete the synthesis of the desired hydroxylated analog, and the analog is then purified. The particular processing and purification steps used to create a specific analog will depend on the exact molecular structure of the desired analog. Such steps are within the ordinary skill of the art, and various examples of suitable reagents and reactions which can be used for such purposes are described below.

ARAD AROMATIC DERIVATIVE SERIES

The class of analogs embodied in the invention are generally represented as:

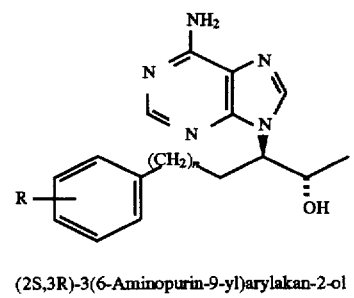

(2S,3R)-3-(6-Aminopurin-9-yl)arylakan-2-ol

Referring to the FIGURE, the following lettered compounds have been synthesized and tested:

TABLE

| Compound | n | R | $K_i$ (M) |
|---|---|---|---|
| 4a | 0 | 4-CH$_3$ | $3.02 \times 10^{-7}$ |
| (2S,3R)-3-(6-Aminopurin-9-yl)-4-(4-methylphenyl)butan-2-ol | | | |
| 4b | 0 | 3-CH$_2$CH$_3$ | $1.33 \times 10^{-7}$ |
| (2S,3R)-3-(6-Aminopurin-9-yl)-4-(3-ethylphenyl)butan-2-ol | | | |
| 4c | 0 | 2-CH$_2$CH$_2$CH$_3$ | $3.02 \times 10^{-7}$ |
| (2S,3R)-3-(6-Aminopurin-9-yl)-4-(2-propylphenyl)butan-2-ol | | | |
| | 1 | H | |
| (2S,3R)-3-(6-Aminopurin-9-yl)-5-phenylpentan-2-ol | | | |

TABLE-continued

| Compound | n | R | $K_i$ (M) |
|---|---|---|---|
| 4d<br>(2S,3R)-3-(6-Aminopurin-9-yl)-5-(3-methylphenyl)pentan-2-ol | 1 | 3-$CH_3$ | $1.02 \times 10^{-9}$ |
| 4e<br>(2S,3R)-3-(6-Aminopurin-9-yl)-6-phenylhexan-2-ol | 1<br>2 | 2-$CH_2CH_3$<br>H | $8.90 \times 10^{-10}$ |
| 4f<br>(2S,3R)-3-(6-Aminopurin-9-yl)-6-(2-methylphenyl)hexan-2-ol | 2 | 2-$CH_3$ | $5.1 \times 10^{-10}$ |
| 4g<br>(2S,3R)-3-(6-Aminopurin-9-yl)-7-phenylheptan-2-ol | 3 | H | $7.60 \times 10^{-10}$ |
| 4h<br>(2S,3R)-3-(6-Aminopurin-9-yl)-8-phenyloctan-2-ol | 4 | H | $9.5 \times 10^{-10}$ |

A generic synthetic scheme is shown in the FIG. 1.

Experimental Procedures

Preparation of compound series 2
GENERAL PROCEDURE 1: (OPENING OF EPOXIDE WITH AROMATIC HALIDES VIA LITHIUM SALTS)

To a stirred solution of aromatic halide (2 eq.) in dry THF cooled to −78° C. (acetone/dry ice bath), was slowly added n-butyl lithium (2 eq.). This mixture was stirred at −78° C. for ½ hour at which time a solution of the epoxide (1 eq.) in dry THF was added followed by the slow addition of boron trifloride etherate (3 eq.). The resulting mixture was stirred at −78° C. for 3 hours, then was allowed to warm to room temperature and stirred overnight. The reaction was then quenched with 2×2 ml saturated aqueous ammonium chloride, concentrated under reduced pressure, and diluted with 200 ml of diethyl ether. The ether layer was washed sequentially with 2×20 ml of brine solution and 1×20 ml of distilled water. The organic phase was dried over magnesium sulfate, filtered and evaporated under reduced pressure to yield the crude product. The crude product was placed on a silica column and eluted with hexane:ethyl acetate (20→10:1) to yield NMR pure desired product.

GENERAL PROCEDURE 2: (OPENING OF EPOXIDE WITH ALIPHATIC HALIDES USING THE GRIGNARD REACTION)

To a mechanically stirred mixture of magnesium metal (2 eq.) and one crystal of iodine in a minimal amount of anhydrous diethyl ether was added drop wise as solution of the aliphatic halide (2 eq.) in anhydrous diethyl ether. When the reaction became vigorous it was cooled in an ice bath while the remaining halide was slowly added. When all of the magnesium has reacted, the solution was cooled to −78° C. (acetone/dry ice bath) and mechanically stirred for 15 min.. A solution of lithium chloride (0.2 eq.) and copper II chloride (0.1 eq.) in a few ml of dry THF was added followed by immediately by the addition of the epoxide (1 eq.) in anhydrous ether. The reaction mixture was stirred at −78° C. for 5 hours then allowed to slowly warm to room temperature and stirred overnight. The reaction was then quenched with 2×2 ml saturated aqueous ammonium chloride, concentrated under reduced pressure, and diluted with 200 ml of diethyl ether. The ether layer was washed sequentially with 2×20 ml of brine solution and 1×20 ml of distilled water. The organic phase was dried over magnesium sulfate, filtered and evaporated under reduced pressure to yield the crude product. The crude product was placed on a silica column and eluted with hexane:ethyl acetate (20→10:1) to yield NMR pure desired product.

(2S,3S)-2-(Benzyloxy)-4-(4-(methylphenyl)butan-3-ol (2a). Was prepared in 82% yield (general procedure 2). $[\alpha]_D$+34.4°(c=1.155,$CHCl_3$) 1H NMR ($CDCl_3$) δ 1.2(d, J=6 Hz,3H) 2.25(s,3H); 2.56–2.85(m,3H); 3.13–3.78(m,2H); 4.16–4.73(qAB,J=12 Hz,2H); 7.03(s,4H); 7.28(s,5H). Anal. Calcd. for $C_{18}H_{22}O_2$: C,79.96;H,8.202. Found: C,79.87;H, 8.12.

(2S,3S)-2-(Benzyloxy)-4-(3-ethenylphenyl)butan-3-ol(2b) was made from 3-bromostyrene using general procedure 1 in 81% yield (a clear gummy liquid).

1H NMR data: δ 1.3 (d, J=6 Hz, 3H), 2.6–3.0 (m, 2H, 1H $D_2O$ exchangeable), 3.3–3.9 (m, 2H), 4.55 (AB quartet center, $\Delta_{AB}$=24 Hz, $J_{AB}$=12 Hz, 2H), 5.25 (d, J=10 Hz, 1H), 5.75 (d, J=18 Hz, 1H), 6.77 (dd, J=18 Hz, 10 Hz, 1H), 7.0–7.6 (m, 9H)

Elemental analysis calcd for $C_{19}H_{22}O_2$ is C, 80.82; H, 7.85. Found: C, 80.60; H, 7.61.

(2S,3S)-2-(Benzyloxy)-4-(2-prop-2-enylphenyl)butan-3-ol (2c) was made from 3(2-bromophenyl)propyl-2-ene using general procedure 1 in 67% yield (a clear gummy liquid).

1H NMR data: δ 1.2 (d, J=6 Hz, 3H), 1.5–1.9 (m, 3H, 1H $D_2O$ exchangeable), 2.7–2.9 (m, 2H), 3.25–3.8 (m, 2H), 4.55 (AB quartet center, $\Delta_{AB}$=21 Hz, $J_{AB}$=12 Hz, 2H), 5.5–7.3 (m, 11H)

Elemental analysis calcd for $C_{20}H_{24}O_2$ is C, 81.04; H, 8.16; Found: C, 81.10; H, 8.34.

(2S,3S)-2-(Benzyloxy)-5-(3-methylphenyl)pentan-3-ol.(2d) Pure was obtained (general procedure 1) in 60% yield: $[\alpha]_D$+16.9° (c=1.285, $CHCl_3$); 1H NMR ($CDCl_3$) δ 1.2 (d, J=6 Hz,3H ); 1.55–1.76 (m, 2H); 2.3 (s, 3H); 2.43–3.03 (m,3H); 3.3–3.55(m,2H); 4.27–4.77 ($J_{AB}$=12 Hz,2H); 6.86–7.45 (m,9H).

Anal.Calcd. for $C_{19}H_{24}O_2$: C,80.24;H,8.505. Found: C,80.37;H,8.36

(2S,3S)-2-(Benzyloxy)-6-phenylhexan-3-ol(2e) was made from 2-phenyl-1-bromoethane using general procedure 2 in 82% yield (a clear gummy liquid).

1H NMR data: δ 1.15 (d, J=6 Hz, 3H), 1.3–1.9 (m, 4H), 2.45–2.7 (m, 2H, 1H $D_2O$ exchangeable), 3.25–3.5 (m, 2H), 4.45 (AB quartet center, $\Delta_{AB}$=24 Hz, $J_{AB}$=12 Hz, 2H), 7.0–7.4 (m 10H).

(2S,3S)-2-(Benzyloxy)-6-(2-methylphenyl)hexan-3-ol(2f) was made from 2-(2-methylphenyl)-1-chloroethane using general procedure 2 in 58% yield (a clear gummy liquid).

Elemental analysis calcd for $C_{20}H_{26}O_2$ is C, 80.50; H, 8.78. Found: C, 80.70; H, 8.82.

(2S,3S)-2-(Benzyloxy)-7-phenylheptan-3-ol(2g) was made from 3-phenyl-1-bromopropane using general procedure 2 in 84% yield (a clear gummy liquid).

1H NMR data: δ 1.1 (d, J=6 Hz, 3H), 1.2–1.65 (m, 6H), 2.35–2.6 (m, 2H, 1H $D_2O$ exchangeable), 3.05–3.4 (m, 4H), 4.55 (AB quartet center, $\Delta_{AB}$=24 Hz, $J_{AB}$=12 Hz, 2H), 6.95–7.3 (m, 10H).

(2S,3S)-2-(Benzyloxy)-8-phenyloctan-3-ol(2h) was made from 4-phenyl-1-chlorobutane using general procedure 2 in 80% yield (a clear gum).

Elemental analysis calcd for $C_{21}H_{28}O_2$ is C, 80.73; H, 9.03. Found: C, 80.61; H, 9.15.

Preparation of compound series 3
GENERAL PROCEDURE: (MITSUNOBU INVERSION ON THE ALCOHOL USING 6-CHLOROPURINE FOLLOWED BY AMONOLYSIS OF THE CRUDE PRODUCT)

To a mixture of the alcohol (1 eq.), triphenylphosphine (2 eq.), and 6-chloropurine (2 eq.) in dry THF was slowly added DIAD (2 eq.). The resulting mixture was stirred at reflux, under nitrogen, overnight. The mixture was then cooled and concentrated under reduced pressure. The residue was applied to a short silica column and eluted with diethyl ether until TLC showed no more product (~500 ml).

The eluted ether was combined and concentrated to about ½ volume under reduced pressure, then was washed with 2×20 ml brine and 1×20 ml distilled water. The organic layer was then dried over magnesium sulfate, filtered and concentrated under reduced pressure to give the crude product. This crude material was then put onto a long silica column and slowly eluted with hexane:ethyl acetate (10:1 to 1:1). Since dihydro DIAD and the product were unable to be completely separated, the mixture was subjected to amonolysis prior to complete purification. Liquid ammonia was added to the crude mixture and placed in a bomb at 60° C. overnight. After this the reaction was diluted with methylene chloride (50 ml) and washed with 3×5 ml of distilled water. The organic phase was dried over magnesium sulfate, filtered and concentrated under reduced pressure. The residue was placed on a silica column and eluted with hexane:ethyl acetate (5:1 to 2:3) to yield the desired product.

(2S,3R)-3-(6-Aminopurin-9-yl)-2-(benzyloxy)-4-(4-methylphenyl)butane(3a) Was prepared in 14.5% yield. (M.P.144°-146° C.). $[\alpha]_D$+106.4° (c=1.91,$CH_2Cl_2$); 1H NMR ($CDCl_3$) d 1.2(d,J=6 Hz,3H); 2.16(s,3H); 3.2–3.43(m, 2H); 3.88–4.76(m,4H); 5.81(bs,2H); 6.83(s,4H); 7.26(s,5H); 7.68(s,1H); 8.23(s,1H).

Anal. Calcd. for $C_{23}H_{25}N_5O$: C,71.29;H,6.503;N,18.07. Found: C,71.14;H,6.70;N,17.89.

(2S,3R)-3-(6-Aminopurin-9-yl)-2-(benzyloxy)-4-(3-ethenylphenyl)butane(3b) was made using general procedure 3 in 11.4% over all yield (a white solid mp. 116°-118° C.).

$^1$H NMR data: δ 1.35 (d, J=6 Hz, 3H), 3.3–3.7 (m, 2H) 4.0–4.2 (m, 1H), 4.55 (AB quartet center, $\Delta_{AB}$=24 Hz, $J_{AB}$=12 Hz, 2H), 4.6–4.9 (m, 1H), 5.1 (d, J=10 Hz, 1H), 5.5 (d, J=18 Hz, 1H) 6.5 (dd, J=18 Hz, 10 Hz, 1H), 6.7–7.2 (m, 4H, 2H $D_2O$ exchangeable), 7.3–7.5 (m, 5H), 7.8 (s, 1H), 8.3, (s, 1H)

Elemental analysis calcd for $C_{24}H_{25}N_5O$ is C, 72.16; H, 6.31; N, 17.53. Found: C, 71.98; H, 6.67; N, 17.74.

(2S,3R)-3-(6-Aminopurin-9-yl)-2-(benzyloxy)-4-(2-prop-2-enylphenyl)butane(3c) was made using general procedure 3 in 9% over all yield.

$^1$H NMR data: δ 1.2 (d, J=6 Hz, 3H), 1.5–1.8 (m, 3H) 2.3–2.6 (m, 3H), 2.8–3.5 (m, 1H), 4.55 (AB quartet center, $\Delta_{AB}$=18 Hz, $J_{AB}$=12 Hz, 2H), 5.35–6.4 (m, 2H, 2H, $D_2O$ exchangeable), 6.8–7.4 (m, 9H), 8.0 (s, 1H), 8.3 (s, 1H)

(2S,3R)-3-(6-Aminopurin-9-yl)-2-(benzyloxy)-5-(3-methylphenyl)pentane(3d) was prepared in 30% yield. (M.P.155°-157° C.). $[\alpha]_D$+52.5° (c=0.415,$CHCl_3$); 1H NMR ($CDCl_3$) d1.2 (d, J=6 Hz,3H); 2.25(s,3H); 2.3–2.48(m,4H); 3.7–4.03(m,1H); 4.18–4.68(m,3H), 5.93(bs,2H); 6.66–7.4 (m,9H); 7.91(s,1H); 8.33(s,1H).

Anal. Calcd. for $C_{24}H_{27}N_5O$: C,71.79;H,6.778;N,17.44. Found: C,71.95;H,6.65;N,17.26

(2S,3R)-3-(6-Aminopurin-9-yl)-2-(benzyloxy)-6-phenylhexane(3e) was made using general procedure 3 in 13% over all yield (a white solid mp 139°-140° C.).

$^1$H NMR data: δ 1.2 (d, J=6 Hz, 3H), 1.3–1.7 (m, 2H), 1.95–2.3 (m, 2H), 2.6 (t, J=8 Hz, 2H), 3.7–3.95, (m, 1H), 4.4 (AB quartet center, $\Delta_{AB}$=24 Hz, $J_{AB}$=12 Hz, 2H), 4.45–4.7 (m, 1H), 6.35 (broad s, 2 H $D_2O$ exchangeable), 6.95–7.35 (m, 10H), 7.9 (s, 1H), 8.3 (s, 1H)

Elemental analysis calcd for $C_{24}H_{27}N_5O$ is C, 71.80; H, 6.78; N, 17.44. Found: C, 71.70; H, 6.89; N, 17.32%.

(2S,3R)-3-(6-Aminopurin-9-yl)-2-(benzyloxy)-6-(2-methylphenyl)hexane(3f) was made using general procedure 3 in 18% over all yield. (two steps) (a white solid mp 141°-142° C.)

(2S,3R)-3-(6-Aminopurin-9-yl)-2-(benzyloxy)-7-phenylheptane(3g) was made using general procedure 3 in 8.3% over all yield. (a white solid mp. 102°-103° C.)

$^1$H NMR data: δ 0.9–1.3 (m, 2H), 1.1 (d, J=6 Hz, 3H), 1.35–1.7 (m, 2H), 1.9–2.25 (m, 2H), 2.35–2.6 (m, 2H), 3.7–3.95 (m, 1H), 4.55 (AB quartet center, $\Delta_{AB}$=24 Hz, $J_{AB}$=12 Hz, 2H), 4.4–4.7 (m, 1H), 6.55 (broad s, 2H $D_2O$ exchangeable), 6.9–7.35 (m, 10H), 7.9 (s, 1H), 8.3 (s, 1H)

(2S,3R)-3-(6-Aminopurin-9-yl)-2-(benzyloxy)-8-phenyloctane(2h) was made using general procedure 3 in 28% over all yield. (a white powder)

Preparation of compound series 4

GENERAL PROCEDURE 4: (REMOVAL OF BENZYL PROTECTING GROUP USING PALLADIUM HYDROXIDE ON CARBON)

A mixture of the adenine derivative (1 eq), palladium hydroxide on carbon (equal in weight to the starting material) in ethanol (20 ml) and cyclohexene (10 ml) was stirred at reflux overnight then allowed to cool to room temperature. The mixture was then filtered and the solution was concentrated under reduced pressure. The residue was placed on a silica column and eluted with hexane:ethyl acetate (1:1) 50 ml, ethyl acetate 50 ml and ethyl acetate: methanol (10:1) to yield the desired product.

(2S,3R)-3-(6-Aminopurin-9-yl)-4-(4-methylphenyl)butan-2-ol.(4a) Was prepared in 65% yield. M.P. 156°-158° C. $[\alpha]_D$ +247.7°(c=0.17,$CHCl_3$); 1H NMR ($CDCl_3$) d 1.33(d, J=6 Hz,3H); 2.16(s,3H); 3.16(d,J=7.5 Hz,2H); 4.05–4.5(m, 3H); 5.8(bs,2H); 6.4–6.9(dd,JAB=9 Hz,4H); 6.98(s,1H); 8.16(s,1H). Anal. Calcd. for $C_{16}H_{19}N_5O.1.5H_2O$: C,59.24;H,6.84;N,21.59. Found: C,59.73;H,6.77;N,21.25

(2S,3R)-3-(6-Aminopurin-9-yl)-4-(3-ethylphenyl)butan-2-ol(4b) was made from MACI-118 using general procedure 4 in 90% yield (a white solid mp. 157°-158° C.).

$^1$H NMR data: δ 1.05 (t, J=8 Hz, 3H), 1.35 (d, J=6 Hz, 3H), 2.45 (q, J=8 Hz, 2H), 3.2 (d, J=6 Hz, 2H), 4.2–4.6 (m, 2H), 4.95 (broad s, 1H $D_2O$ exchangeable) 6.5–7.2 (m, 4H, 2H $D_2O$ exchangeable), 7.5 (s, 1H), 8.2, (s, 1H).

Elemental analysis calcd for $C_{17}H_{21}N_5O$ is C, 65.57; H, 6.80; N, 22.49. Found: C, 65.78; H, 7.00; N, 22.36.

(2S,3R)-3-(6-Aminopurin-9-yl)-4-(2-propylphenyl)butan-2-ol(4c) was made using general procedure 4 in 91% yield (a white solid mp 181°-182° C.).

$^1$H NMR data: δ 0.8 (t, J=9 Hz, 3H), 1.15–1.6 (m, 5H), 2.3 (t, J=9 Hz, 2H), 3.1–3.4 (m, 2H), 3.75 (broad s, 2H $D_2O$ exchangeable), 7.25 (s, 1H), 8.1 (s, 1H)

Elemental analysis calcd for $C_{18}H_{23}N_5O$ is C, 66.44; H, 7.12; N, 21.52. Found: C, 66.03; H, 7.40; N, 20.36.

(2S,3R)-3-(6-Aminopurin-9-yl)-5-(3-methylphenyl)pentan-2-ol(4d) was prepared in 62% yield. M.P.146°-148° C.[α]$_D$+55.9° (c=0.315,$CHCl_3$); 1H NMR ($CDCl_3$) d1.21(d,J=6 Hz,3H); 2.28(s,3H); 2.33–2.68(m,4H); 4.03–4.46(m,2H); 4.95(bs,1H); 6.5(bs,2H); 6.75–7.09(m, 4H); 7.76(s,1H); 8.26(s,1H).

Anal. Calcd. for $C_{17}H_{21}N_5O$: C,65.57;H,6.797;N,22.49. Found: C,65.38;H,6.92;N,22.62

(2S,3R)-3-(6-Aminopurin-9-yl)-6-phenylhexan-2-ol(4e) was made using general procedure 4 in 98% yield (a white solid mp. 153°-154° C.)

$^1$H NMR data: δ 1.15 (d, J=6 Hz, 3H), 1.2–1.6 (m, 2H), 1.7–2.2 (m, 2H), 2.4–2.7 (m, 2H), 3.95–4.5 (m, 2H, 1H $D_2O$ exchangeable), 6.6–7.25 (m 5H, 2H $D_2O$ exchangeable), 7.8 (s,1H), 8.2 (s, 1H)

Elemental analysis Calcd for $C_{17}H_{21}N_5O$ is C,65.57; H,6.8; N,22.49. Found C, 65.65; H, 6.89; N,22.60%.

(2S,3R)-3-(6-Aminopurin-9-yl)-6-(2-methylphenyl)hexan-2-ol(4f) was made using general procedure 4 in 71% yield (a white solid mp 153°-155° C.).

(2S,3R)-3-(6-Aminopurin-9-yl)-7-phenylheptan-2-ol(4g) was made using general procedure 4 in 92% yield (a gummy solid).

$^1$H NMR data: d 0.9–1.7 (m, 7H), 1.7–2.1 (m, 2H), 2.1–2.5 (m, 2H), 3.9–4.4 (m, 2H), 4.8 (broad s, 1H D$_2$O exchangeable), 6.6–7.2 (m, 5H, 2H D$_2$O exchangeable), 7.75 (s, 1H), 8.1 (s, 1H)

(2S,3R)-3-(6-Aminopurin-9-yl)-8-phenyloctan-2-ol(4h) was made using general procedure 4 in 89% yield. (a gummy solid)

Biological Evaluation

The compounds were tested as inhibitors of calf intestinal mucosa adenosine deaminase (ADA). Deamination of adenosine to inosine at 25° C. was measured directly from the decrease in absorbance at 265 nm. (Kalckar, H. M., Differential Spectrophotometry of Purine Compounds by Means of Specific Enzymes, III Studies of the Enzymes of Purine Metabolism, *J. Biol. Chem.*, 1947, 167, 461–475 and Agarwal, R. P.; Parks, R. E., Jr., Adenosine Deaminase from Human Erythrocytes, *Method Enzymol*, 1978, 51, 502–507) ADA (Type VI), adenosine were purchased from Sigma Chemical Co., St. Louis, Mo. The enzyme was diluted into a stabilizing buffer of 50 mM potassium phosphate, pH 7.2. Varying concentrations of analogs were preincubated for 3 min. with 20 µL of ADA solution in a total volume of 2 mL of phosphate buffer. This permitted the association reaction between the enzyme and a semi-tight-binding inhibitor to reach a steady state, Agarwal, R. P.; Spector, T.; Parks, R. E., Jr., Tight-Binding Inhibitors-IV, Inhibition of Adenosine Deaminase by Various Inhibitors, Biochem. Pharmacol., 1977, 26, 359–367. Reactions were started by the addition of 0.1 mL of substrate (final concentrations: 0.015 unit/mL ADA, 50 µM adenosine, 50 mM phosphate). The K$_i$ values were determined from nonlinear regression analysis of the velocity vs. inhibition concentration (1) curves using the computer program (Delta Point-Delta Graph Pro 3) for the equation $v_o$–$v_o$ 1/K$_i$ (1+S/K$_m$)+1], where $v_o$ is the reaction rate in the absence of inhibitor. The Km for adenosine, determined at 10–72 µM concentrations under identical conditions, was 25 µM.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A compound of:

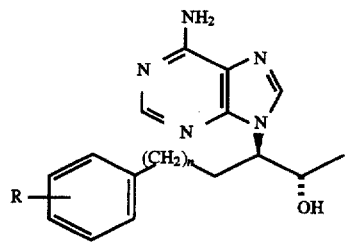

where n=0–4 and R is selected from the group consisting of 4—CH$_3$; 3—CH$_2$CH$_3$; 2—CH$_2$CH$_2$CH$_3$; H; 3—CH$_3$; 2—CH$_2$CH$_3$; [H] 2—CH$_3$.

2. The compound of claim 1 wherein n=0, R=4—CH$_3$.

3. The compound of claim 1 wherein n=0, R=3—CH$_2$CH$_3$.

4. The compound of claim 1 wherein n=0, R=2—CH$_2$CH$_2$CH$_3$.

5. The compound of claim 1 wherein n=1, R=H.

6. The compound of claim 1 wherein n=1, R=3—CH$_3$.

7. The compound of claim 1 wherein n=1, R=2—CH$_2$CH$_3$.

8. The compound of claim 1 wherein n=2, R=H.

9. The compound of claim 1 wherein n=2, R=2—CH$_3$.

10. The compound of claim 1 wherein n=3, R=H.

11. The compound of claim 1 wherein n=4, R=H.

12. A composition comprising a compound of claim 1; or a pharmacologically acceptable salt thereof; or a pharmacologically acceptable isomer thereof which inhibit adenosine deaminase activity with a Ki value between about $10^{-7}$ and about $10^{-10}$; or a combination of the same.

* * * * *